(12) United States Patent
Nelson

(10) Patent No.: US 6,302,990 B1
(45) Date of Patent: Oct. 16, 2001

(54) METHOD OF MAKING A LINED INFUSION CATHETER

(75) Inventor: Timothy S. Nelson, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/517,525

(22) Filed: Mar. 2, 2000

Related U.S. Application Data

(60) Continuation of application No. 08/924,343, filed on Sep. 5, 1997, now abandoned, which is a division of application No. 08/385,498, filed on Feb. 8, 1995, now Pat. No. 5,702,372.

(51) Int. Cl.[7] ................................................. A61M 25/00
(52) U.S. Cl. ............... 156/244.13; 156/242; 156/244.11; 156/293; 600/435; 604/529
(58) Field of Search .......................... 156/244.11, 244.13, 156/242, 245, 244.24, 244.26, 293, 294; 604/529; 600/435

(56) References Cited

U.S. PATENT DOCUMENTS

| | | |
|---|---|---|
| 3,605,750 * | 9/1971 | Sheridan et al. ..................... 604/529 |
| 3,879,516 | 4/1975 | Wolvek . |
| 3,926,705 | 12/1975 | Todd . |
| 4,186,745 | 2/1980 | Lewis et al. . |
| 4,300,244 | 11/1981 | Bokros . |
| 4,551,292 | 11/1985 | Fletcher et al. . |
| 4,778,455 * | 10/1988 | Kousai et al. ..................... 604/529 |
| 4,796,637 | 1/1989 | Mascuch et al. . |
| 4,798,597 | 1/1989 | Vaillancourt . |
| 4,806,182 | 2/1989 | Rydell et al. . |
| 4,838,876 | 6/1989 | Wong et al. . |
| 4,846,812 | 7/1989 | Walker et al. . |
| 4,943,560 | 7/1990 | Wigness et al. . |
| 4,983,169 | 1/1991 | Furukawa . |
| 4,990,155 | 2/1991 | Wilkoff . |
| 4,994,047 | 2/1991 | Walker et al. . |
| 4,999,210 | 3/1991 | Solomon et al. . |
| 5,041,100 | 8/1991 | Rowland et al. . |
| 5,049,138 | 9/1991 | Chevalier et al. . |
| 5,066,278 | 11/1991 | Hirschberg et al. . |
| 5,066,285 | 11/1991 | Hillstead . |

(List continued on next page.)

FOREIGN PATENT DOCUMENTS 0 448 886 A1   12/1990   (EP) .
0 473 045 A1    8/1991   (EP) .

Primary Examiner—Jeff H Aftergut
(74) Attorney, Agent, or Firm—Curtis D. Kinghorn; Eric R. Waldkoetter; Tom Berry

(57) ABSTRACT

An infusion catheter for delivering drugs or other agents to selected sites in an organism, such as a human. In an alternate embodiment, a catheter system is disclosed having an infusion catheter and a pump that may be implanted or disposed outside the organism. In either embodiment, the free end of the catheter bears a rounded tip that has at least one elution hole for discharging an agent or drug to a selected site. The catheter has a tubular inner liner that is integral with the tip. The inner liner and tip are formed from a drug compatible polymeric material that is relatively nonporous and unreactive with the agent to be infused. A biocompatible flexible elastomeric tubular jacket surrounds the inner liner and a portion of the tip excluding that portion containing the elution hole or holes. Since the agent flowing in the catheter is isolated from the jacket while flowing through the catheter, and since the inner liner is relatively nonporous and unreactive with the agent to be used, the agent is prevented from diffusing out of the catheter, adsorbing to the surface of the biocompatible jacket, reacting adversely with the jacket material or becoming exposed to substances diffusing through the jacket.

10 Claims, 7 Drawing Sheets

U.S. PATENT DOCUMENTS

| | | |
|---|---|---|
| 5,171,305 | 12/1992 | Schickling et al. . |
| 5,199,427 | 4/1993 | Strickland . |
| 5,201,724 | 4/1993 | Hukins et al. . |
| 5,203,776 | 4/1993 | Durfee . |
| 5,218,957 | 6/1993 | Strickland . |
| 5,234,416 | 8/1993 | Macaulay et al. . |
| 5,244,619 | 9/1993 | Burnham . |
| 5,255,675 | 10/1993 | Kolobow . |
| 5,342,383 * | 8/1994 | Thomas .................................. 604/529 |
| 5,348,536 | 9/1994 | Young et al. . |
| 5,401,257 | 3/1995 | Chevalier et al. . |
| 5,415,636 | 5/1995 | Forman . |

* cited by examiner

METHOD OF MAKING A LINED INFUSION CATHETER

This application is a Continuation of application Ser. No. 08/924,343 filed Sep. 5, 1997 now abandoned, which is a Divisional application of Ser. No. 08/385,498 filed Feb. 8, 1995 now U.S. Pat. No. 5,702,372.

BACKGROUND OF THE INVENTION

1. Field of the Invention

In general, this invention relates to infusion catheters. More specifically, this invention relates to an infusion catheter for delivering fluid into an organism where the catheter has a non-reactive lining and tip, surrounded partially by a flexible silicone-type material.

2. Description of the Related Art

When chronic administration of a pharmaceutically active agent is required, internal delivery by an external infusion pump or an implantable infusion pump ("IIP"), in combination with a catheter, may be the desired delivery means. For example, IIP-catheter delivery may be preferred when, for example, the site specific delivery of the drug is critical, or the drug must be administered in tightly controlled, yet minute dosages.

In applications where the quantity of delivered drug is relatively minute and must be carefully tailored, it may be critical that the delivered drug be non-reactive with the material of the catheter. Non-reactive means that the delivered drug flows from the IIP to the delivery site without adhering to, diffusing through, or otherwise chemically reacting with, the catheter itself. Standard delivery catheters normally comprise a single tubular member and are composed of a flexible elastomeric material, typically silicone, that is biocompatible with the animal body into which the desired agent is delivered. A more recent design includes an internal lining that is more compatible with the agent desired to be delivered while maintaining the biocompatibility of the external catheter sheath.

FIG. 1 depicts a portion of a typical prior art implantable catheter 10 with a drug compatible internal lining. Catheter 10 comprises a tubular jacket or sheath 12 that is coupled at one end to the IIP (not shown) and terminates at its other end in a rounded tip 14. One or more elution holes 16 are disposed in sheath 12 proximate the rounded tip 14. Sheath 12 is ordinarily tubular and manufactured from a flexible biocompatible elastomeric material such as silicone. It is desirable for sheath 12 to be both flexible and biocompatible. A flexible material makes catheter 10 easier to conform to the various curved passageways in the body during placement and use. The biocompatibility of sheath 12 will enable catheter 10 to remain in the body for prolonged periods of time without prompting an immune system response. The interior of sheath 12 is lined with a tubular lining 18 which is coextensive with sheath 12 from the IIP (not shown) to a sheath/lining seal point 20. Catheter 10 may not be manufactured solely of this material because the material may often be too rigid to make a usable catheter for actual use. Sheath/lining seal point 20 is ordinarily located a few millimeters from the elution holes 16. The lining 18 is ordinarily fabricated from a material that will be non-reactive with the delivered agent such as polyethylene, polyurethane or polytetraflouroethylene (PTFE) or TEFLON® as it is commonly known in the trade.

If the delivered drug is sensitive to the material of sheath 12, the delivered drug may either be adsorbed by sheath 12, diffuse across sheath 12 or react chemically with sheath 12 or with substances diffusing through sheath 12 from outside catheter 10. For example, if the delivered drug is adsorbed by sheath 12, the amount of delivered drug may be significantly less than the required dosage. Similarly, if undesirable agents diffuse through sheath 12 and react with the delivered drug, the amount and efficacy of the delivered drug may be compromised. Because the seal point 20 is directly exposed to the delivered drug, there is the potential for undesirable seepage of the drug between sheath 12 and lining 18.

Many drugs or agents exhibit some detrimental sensitivity to silicone or drugs or agents that may diffuse through a silicone sheath. Insulin presents one example. In certain circumstances, carbon dioxide may diffuse through a silicone sheath. If insulin is flowing through catheter 10, carbon dioxide from outside catheter 10 may diffuse through sheath 12 and react with the buffer in the insulin solution, causing a pH change in the insulin solution. As a result, the insulin buffer breaks down, causing degradation and polymerization of the insulin to occur. In some applications involving the chronic dispensing of insulin, suitable buffers to counteract the pH changes brought on by $CO_2$ diffusion are simply not feasible.

Another example of drugs sensitive to silicone is presented by neurotrophic factors such as nerve growth factor (NGF), brain-derived neurotrophic factor (BDNF), ciliary neurotrophic factor (CNTF), or glial-derived neurotrophic factor (GDNF), currently being studied as potential therapies for amyotrophic lateral sclerosis, Parkinson's Disease, or other neurological disorders. The particular neurotrophic factor may either be adsorbed by the interior surface of the silicone sheath 12, or alternatively react with the silicone sheath 12 and degrade into secondary components. The dosage levels for such neurotrophic factors may be so small that an appreciable loss or degradation of the delivered agent will adversely effect the agent's ability to satisfactorily treat the patient.

In the prior art catheter 10 shown in FIG. 1, extension of the lining 18 past the elution holes 16 has proved to be impractical, since it has been difficult, if not impossible, to adequately seal the interfaces between sheath 12 and lining 18 that are in fluid communication with the elution holes 16. The present invention is directed to solving one or more of the above-noted problems.

SUMMARY OF THE INVENTION

In one aspect of the present invention a catheter is provided. The catheter includes an elongated inner liner that has an open first end, a distal end that has at least one opening, and a first length. An elongated jacket is disposed about the inner liner and has a second length less than the first length whereby fluid flowing in the inner liner is isolated from the jacket. The problems associated with the infused drug or agent being sensitive to the material of the jacket are eliminated by making the inner liner completely coextensive with the interior of the jacket.

In another aspect of the present invention, a catheter system for delivering agents, drugs or other fluids to a selected site within an organism is provided. The system has a catheter and a pump coupled to the catheter for delivering the fluid to the catheter. The catheter is the novel catheter described above and in more detail hereafter with the catheter additionally being in fluid communication with the pump. The jacket, disposed about the inner liner, extends from the pump to the distal end of the catheter and is isolated from fluid flowing in the inner liner.

The invention will now be described in detail with reference to the accompanying drawings where like elements, wherever referred to, are referred to with like reference numbers.

BRIEF DESCRIPTION OF THE DRAWINGS

Advantages of the invention will become apparent upon reading the following detailed description and references to the drawings in which.

DESCRIPTION OF THE PREFERRED EMBODIMENT

Figure 1:
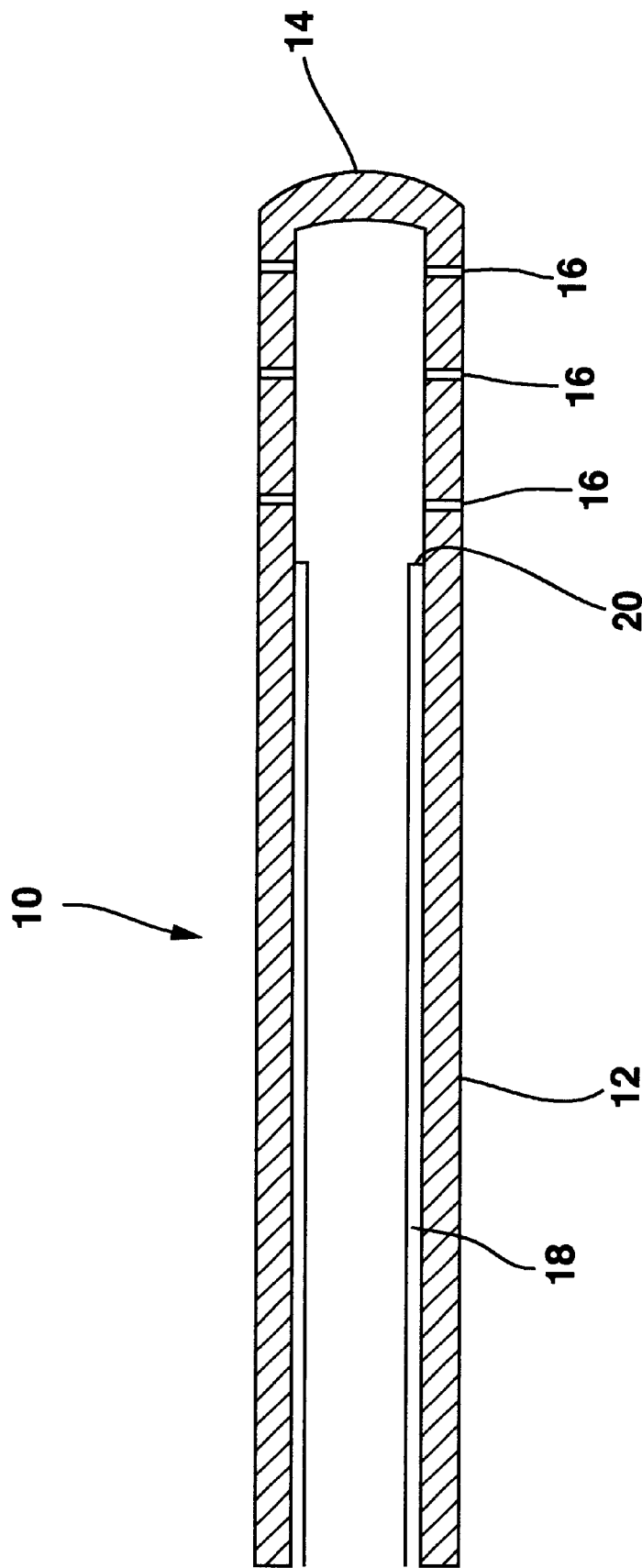
FIG. 1 is a sectional view of the distal end of a prior art catheter.
Figure 2:
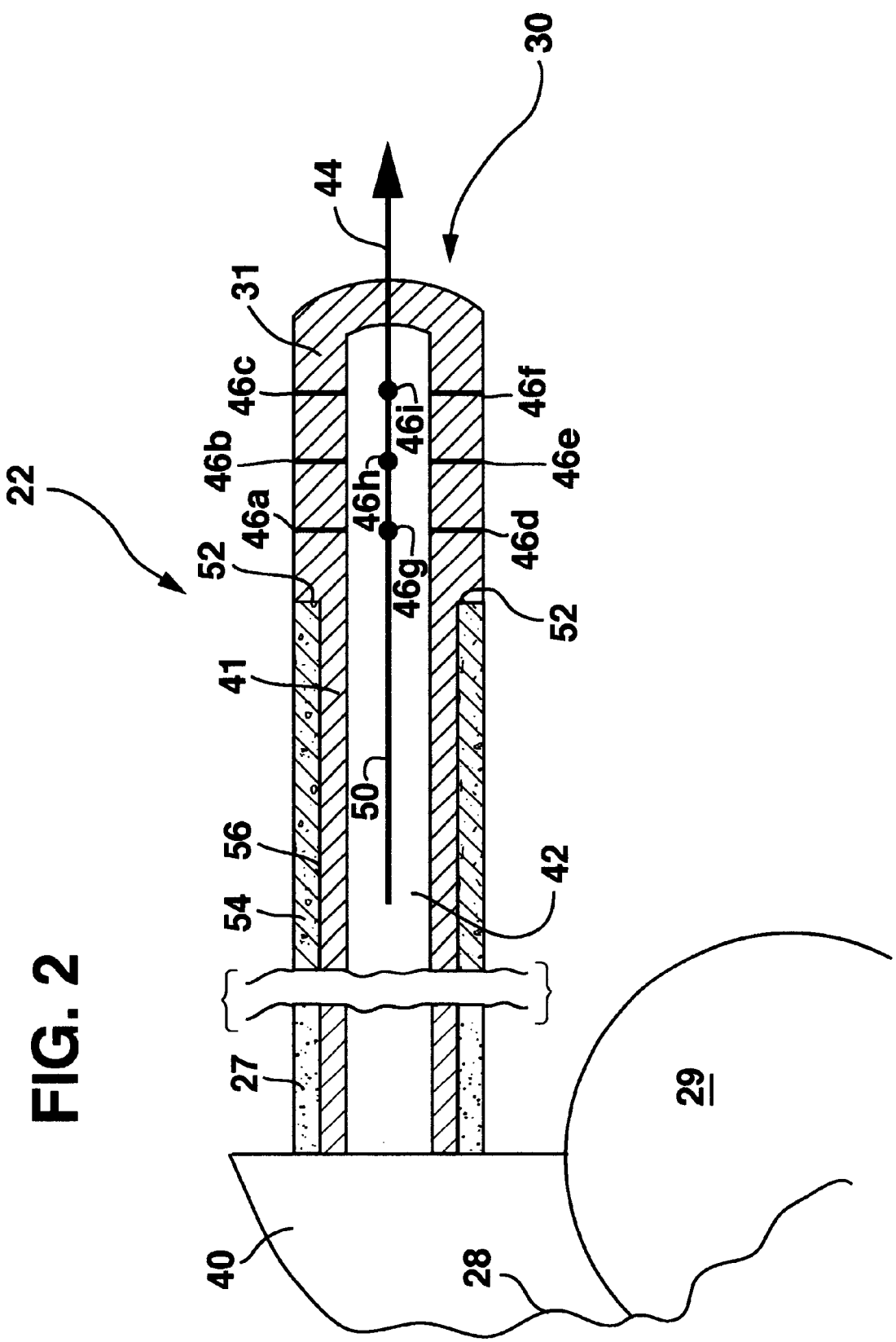
FIG. 2 is a section view of a preferred embodiment of the distal end of the catheter.

A catheter system 22 is disclosed that may be understood by reference to the Figures, particularly FIG. 2. Catheter system 22 includes a catheter 27 and an implantable infusion pump (IIP) 29. Catheter 27 has a proximal end 28 and a distal end 30. FIG. 2 depicts a preferred embodiment of catheter system 22 where catheter 27 and distal end 30 are shown in an enlarged sectional view and with IIP 29 shown in a partial cut-away view. The size of catheter 27 and distal end 30 are highly exaggerated for ease of illustration of the structure thereof and the full length of catheter 27 is not shown for simplicity of illustration. Proximal end 28 of catheter 27 is coupled to a pump connector 40 that is in fluid communication with IIP 29. The connection between catheter 27 and pump connector 40 is shown schematically in FIG. 2. It should be understood that the actual type of connection between pump connector 40 and catheter 27 will vary depending upon the particular type of IIP utilized.

Catheter 27 includes an elongated inner liner 41 that extends from pump coupling 40 and terminates at distal end 30 in a tip 31. Liner 41 forms a lumen 42 through which the selected agent, drug or other fluid is delivered to the patient at tip 31. Liner 41 and tip 31 are preferably integrally molded, though, as discussed below, they may be fabricated as separate units and later coupled. Tip 31 has a generally rounded end 44 to minimize tissue disruption during insertion.

At least one elution hole 46 is formed through tip 31. In the preferred embodiment, one to several elution holes 46a–i extend from lumen 42 of catheter 27 through the walls of tip 31 to enable fluid to flow from lumen 42 through elution holes 46a–i and into the particular site within the body. There are three elution holes that are collinear with holes 46g–i that are not shown because distal end 30 is shown in half section. Elution holes 46a–i are depicted as being disposed approximately normal to the longitudinal axis 50 of catheter 27. However, it should be understood that elution holes 46a–i may be disposed at other angular geometries as well. It should be further understood that, while tip 31 must have at least one elution hole to deliver an agent to the body, the actual number of holes will depend upon the agent, drug or fluid to be delivered, and the particular delivery site within the body. In a preferred embodiment, elution holes 46a–i are cylindrical and have a diameter of approximately 0.016". Because it is possible to have a difference in external diameters of tip 31 and inner liner 41, there may be a peripheral shoulder 52 formed at the junction between inner liner 41 and tip 31.

It is desirable that inner liner 41 be relatively flexible, compatible, and generally non-reactive with the particular agent, drug or fluid to be infused. Catheter 27 may not be manufactured solely of this lining material because the material may often be too rigid to make a usable catheter for actual use. Rigidity problems that may be inherent in the material of inner liner 41 are not an issue to the overall stiffness of catheter 27 if only tip 31 and the relatively thin inner liner 41 are made from the rigid material. While the particular material for inner liner 41 used will depend on the agent, drug or other fluid infused, some possible materials are nonporous polyethylene, polytetraflouroethylene (PTFE) or TEFLON® as it is commonly known in the trade, and polyurethane. It is important that the material used to form inner liner 41 be relatively nonporous to avoid the potential of contaminants, such as $CO_2$, diffusing from the organism into lumen 42.

An elongated jacket or jacket 54 surrounds inner liner 41. Jacket 54 extends from coupling 40 to shoulder 52 on tip 31. There is preferably a relatively tight tolerance between the external diameter of inner liner 41 and the internal diameter of jacket 54. In a preferred embodiment, the tolerance is approximately 0.005".

Jacket 54 is preferably formed of a flexible biocompatible substance that is relatively non-porous. The biocompatible substance utilized for making up jacket 54 may include silicone, barium loaded silicone, polyurethane, polyether urethane, polyether urethane urea, styrene butadiene rubber and other related flexible biocompatible polymers. Presently, silicone is the preferred material for jacket 54.

Jacket 54 is secured to inner liner 41 by a suitable adhesive applied to the interface 56 between the outer surface of inner liner 41 and the inner surface of jacket 54. The adhesive is applied along the entire length of interface 56 as well as shoulder 52 and the portion of jacket 54 abutting shoulder 52. The adhesive is preferably a biocompatible medical silicone adhesive suitable to bond the silicone elastomer to the inner liner. Other types of adhesives are suitable as well such as, for example, medical grade urethane. Ultimately, the particular type of adhesive used will depend upon the materials used to form jacket 54 and inner liner 41.

In the embodiment of the invention shown in FIG. 2, the drug delivered through catheter 27 never contacts the adhesive that binds liner 41 to jacket 54 since the adhesive is "sealed" between inner liner 41 and jacket 54. Further, in this embodiment, a continuous surface is provided along the entire length of inner lumen 42 of catheter 27. As a result, there are no crevices, cracks, breaks or discontinuities along inner lumen 42 for the agent, drug or fluid being delivered to invade. If the agent, drug or fluid were to invade a crack or similar break in inner liner 41, the agent, drug or fluid could be contaminated by either the adhesive that binds inner liner 41 to jacket 54 or by gases or other materials that might diffuse through jacket 54 from outside jacket 54. The contaminated agent, drug or other fluid would then contaminate the remaining agent, drug or fluid in lumen 42.

The actual thickness of the walls of inner liner 41 and jacket 54 will depend upon the particular environment where the catheter will be used. Ordinarily, the wall thickness of inner liner 41 will be relatively less than the wall thickness of jacket 54. However, if inner liner 41 is composed of a sufficiently flexible material, it may have a wall thickness relatively larger than the wall thickness of jacket 54.

Figure 3:
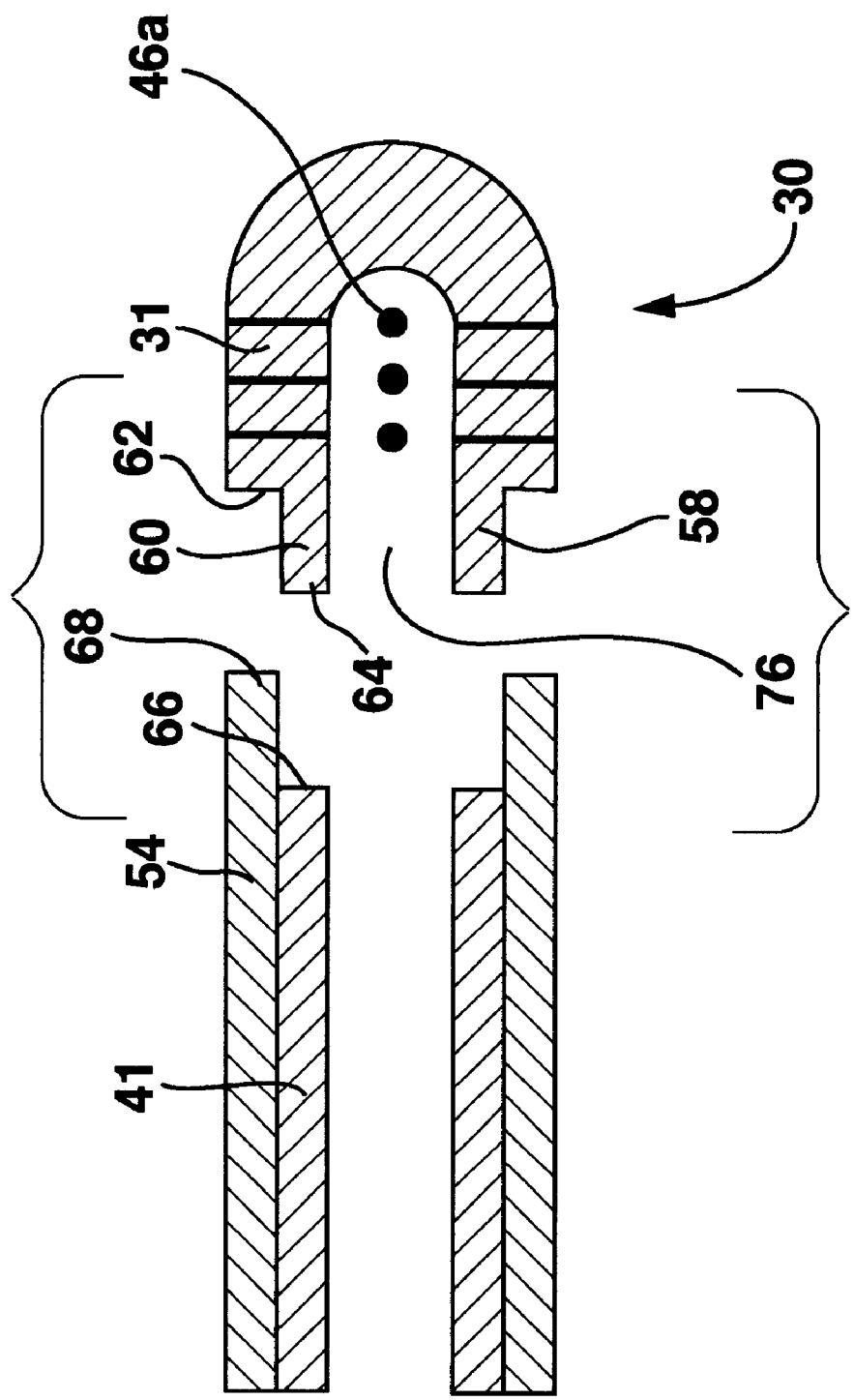
FIG. 3 depicts a sectional view of an alternate preferred embodiment of the distal end of the catheter.

FIG. 3 depicts an alternate preferred embodiment of distal end 30. In this embodiment, tip 31 is not molded integrally with inner liner 41, but rather is formed as a separate piece that is fixed to inner liner 41 and jacket 54 by a suitable biocompatible adhesive. The agent, drug or other fluid still exits tip 31 through orifices 46 located near the distal end 30 of tip 31. Tip 31 has a cylindrical nipple portion 58 that has an outer peripheral surface 60 with approximately the same external diameter as the external diameter of inner liner 41. Nipple portion 58 also has a peripheral shoulder 62 with an external diameter greater than the external diameter of outer peripheral surface 60 and a front peripheral surface 64 that extends at a right angle to outer peripheral surface 60. A tip lumen 76 extends from front peripheral portion 64 through nipple portion 58 to orifices 46. Tip lumen 76 has an inner diameter equal to the inner diameter of inner liner 41.

When tip 31 is mated with inner liner 41 and jacket 54, front peripheral surface 64 abuts peripheral surface 66 on inner liner 41 and peripheral shoulder 62 abuts peripheral surface 68 on jacket 54. A continuous lumen is formed from the proximal end of inner liner 41 to orifices 46. Because orifices 46 pass through the material of tip 31 that is the same material as inner liner 41 and because this material is non-reactive to the-agent, drug or fluid passing through catheter 27, the agent, drug or other fluid contacts only the non-reactive material lining of catheter 27.

To secure tip 31 to the rest of catheter 27, a suitable biocompatible adhesive, such as the type disclosed above, is applied to front peripheral surface 64, outer surface 60, and peripheral shoulder 62 before the parts are joined.

Because jacket 54 is physically isolated from lumen 42 of catheter 27 by integrally formed or coupled inner liner 41 and tip 31, agents, drugs or other fluids passing through lumen 42 that may be sensitive to the material of jacket 54 are not exposed to jacket 54 while flowing through lumen 42 and ultimately discharging out of elution holes 46a–i. As a result, the infused agent, drug or other fluid is exposed only to the agent, drug or other fluid non-reactive material of inner liner 41 and tip 31. Furthermore, there is no joint or seal point between inner liner 41 and jacket 54 that is exposed to the agent, drug or fluid flowing through catheter 27 that might lead to undesirable seepage through jacket 54.

Catheter 27 is ordinarily fabricated in the following two fashions depending on whether tip 31 is integrally molded with inner liner 41 or not. If tip 31 is integrally molded with inner liner 41, inner liner 41 is extruded with an integral tip 31. Next, jacket 54 is extruded. Tip 31 may then be molded or otherwise manipulated to the desired configuration. A suitable biocompatible adhesive is applied to the outer surface of inner liner 41 and jacket 54 is slid over inner liner 41.

If tip 31 is not to be integrally molded with inner liner 41, inner liner 41 is extruded without an integral tip 31. Tip 31 is then separately extruded, molded or otherwise formed. If tip 31 is extruded, tip 31 may then be molded to the desired configuration. Next, jacket 54 is extruded. A suitable biocompatible adhesive is applied to the outer surface of inner liner 41 and jacket 54 is slid over inner liner 41. The final step entails coupling tip 31 to inner liner 41 and jacket 54 using a suitable biocompatible adhesive. The suitable biocompatible adhesive is applied to front peripheral surface 64, outer surface 60, and peripheral shoulder 62 before these parts are joined with jacket 54 and inner liner 41.

Figure 4:
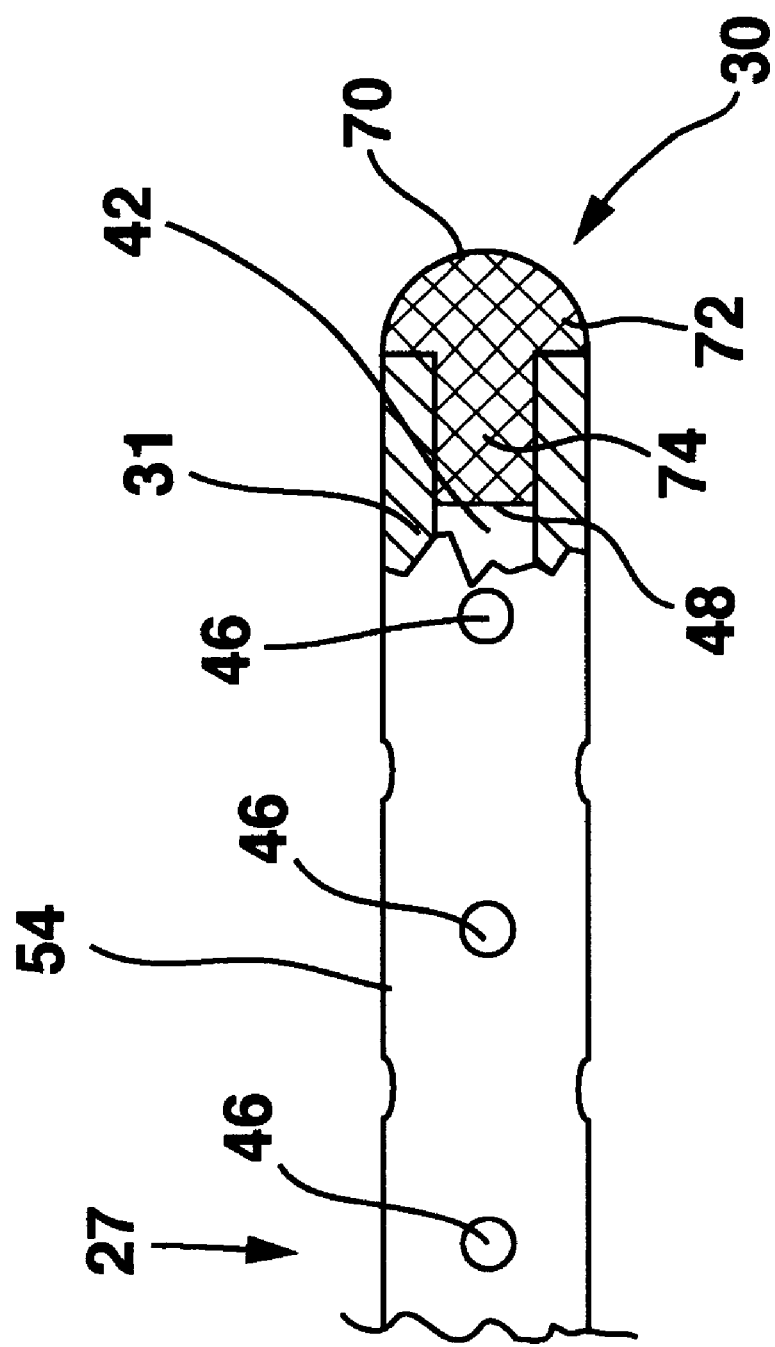
FIG. 4 depicts a partial sectional view of a preferred embodiment of the catheter of FIG. 2 with a radiographic marker tip.

FIG. 4 depicts an alternate preferred embodiment of distal end 30 of catheter 27 where a radiographic marker 70 is coupled to tip 31. Radiographic marker 70 renders at least a portion of tip 31 opaque to x-rays, enabling tip 31 to be observed during fluoroscopy or via x-ray to facilitate placement of distal end 30 and tip 31. In a preferred embodiment, radiographic marker 70 comprises a semispherical portion 72 that has a cylindrical nipple 74 emanating away therefrom. Semispherical portion 72 provides a rounded profile for minimizing tissue disruption during insertion. Cylindrical nipple 74 is sized to fit snugly within lumen 42 and be held in place via a suitable biocompatible adhesive, such as those discussed above.

In a preferred embodiment, radiographic marker 70 comprises tantalum powder dispersed in a matrix composed of a biocompatible adhesive, such as the ones discussed above. The preferred ratio of tantalum to adhesive is 3 to 1. Ordinarily, radiographic marker 70 will be premolded prior to insertion into lumen 42. After radiographic marker 70 has been inserted into lumen 42, a thin coating of the same biocompatible adhesive is preferably applied to the exterior of semispherical portion 72. Other materials may also be suitable for the radiographic marker 70, such as barium or similar materials.

Alternatively, radiographic marker 70 may be composed of a material that is sensitive to nuclear magnetic resonance imaging (MRI) to enable tip 31 to be detected during an MRI scan. A preferred material for radiographic marker 70 in this embodiment is platinum, although tantalum, cobalt, and similar materials are also suitable. Regardless of whether radiography or MRI is being utilized, the goal of providing a radiographic marker 70 is to enable the operator to accurately detect the precise location of tip 31 to facilitate placement and later verification of the integrity and position of catheter 27.

Figure 5:
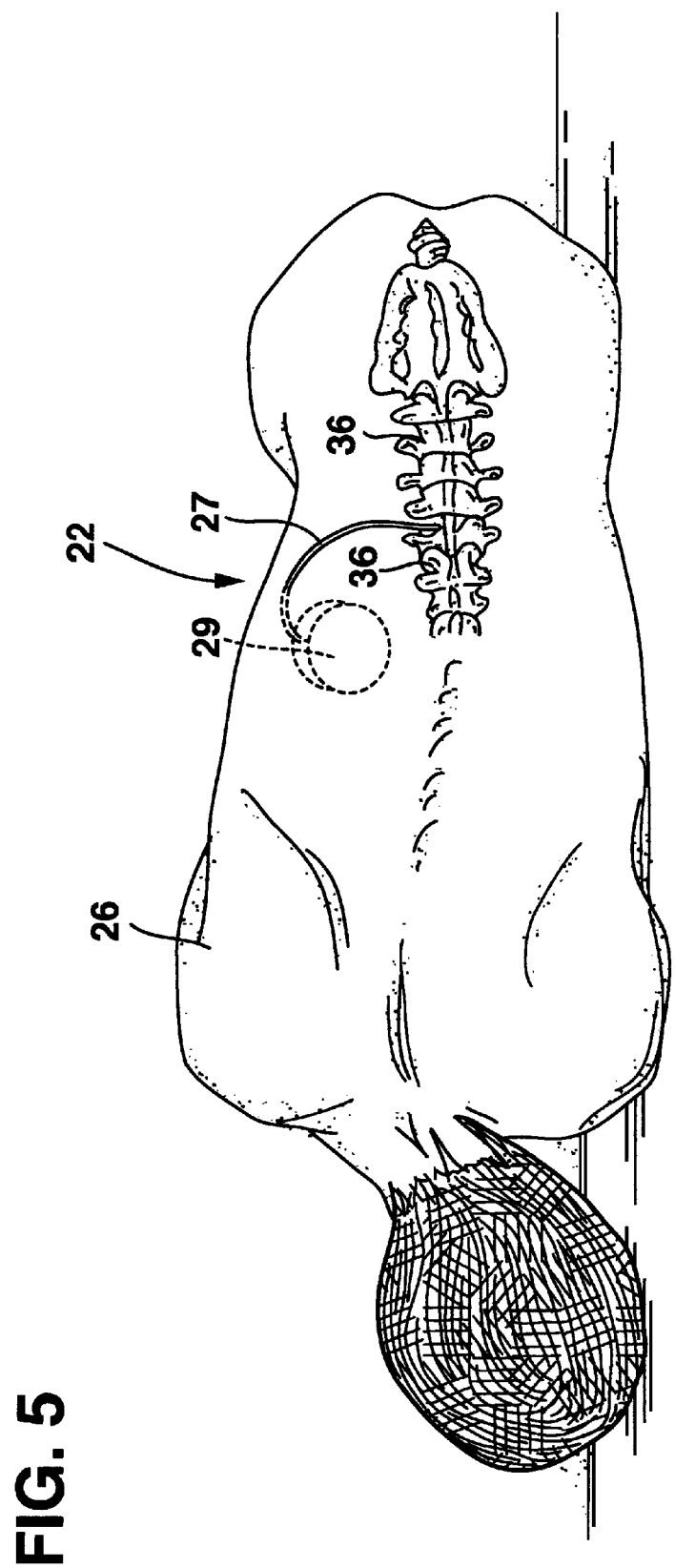
FIG. 5 depicts a preferred embodiment of the catheter system showing one possible implantation in a human body.
Figure 6:
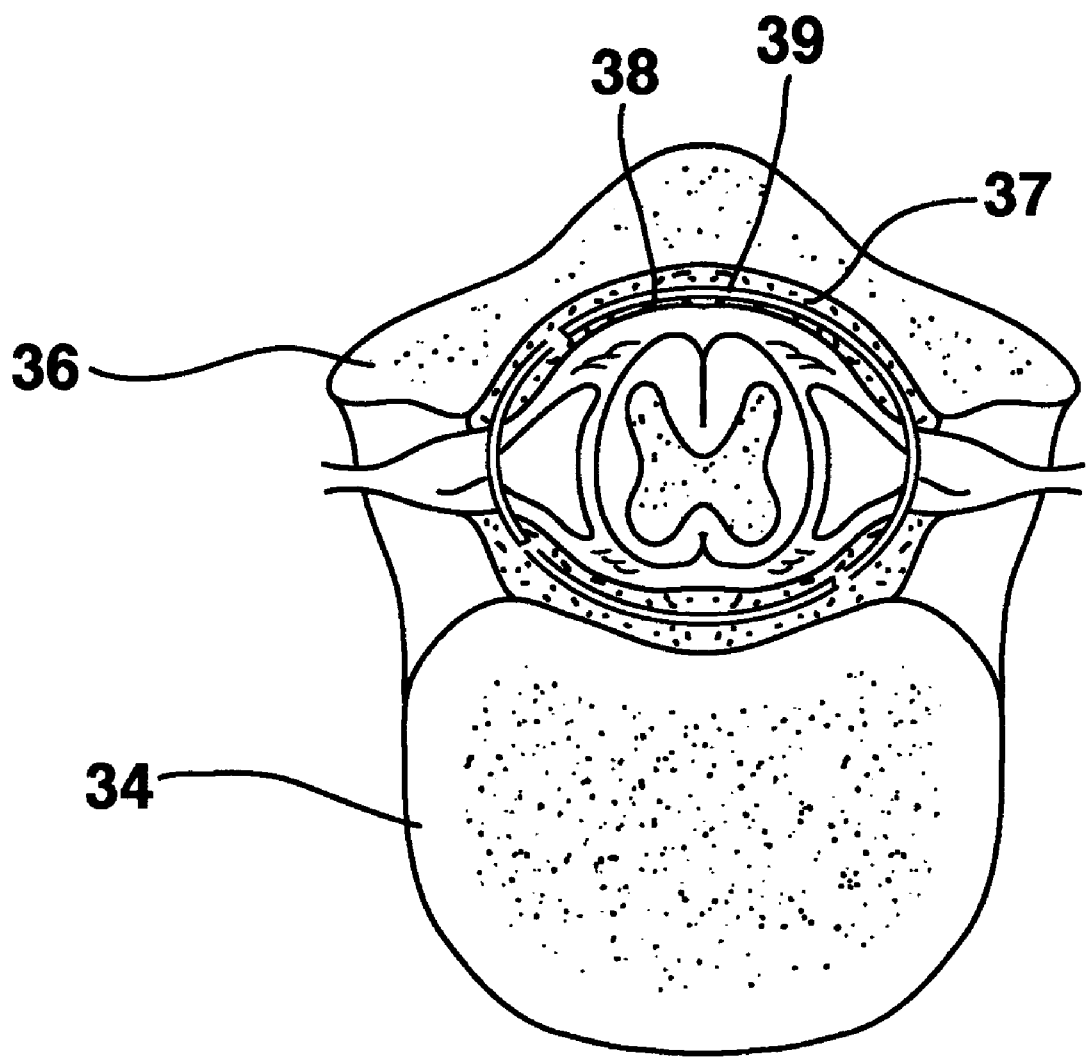
FIG. 6 is a sectional view of a typical spinal column.

FIGS. 5 and 6 depict an application of catheter system 22 for infusing neurological or analgesic agents, drugs or other fluids directly into the spinal column of the body 26. FIG. 5 shows the general placement of catheter system 22 in relation to the body 26. FIG. 6 is a cross-sectional view of the spinal column 34 of the body 26 that shows some potential infusion sites. In FIGS. 5 and 6, distal end 30 and tip 31 are obscured by vertebrae 36. An Implantable Infusion Pump (IIP) 29 is surgically implanted subcutaneously in the abdominal region of the body 26. Catheter 27 is tunnelled subcutaneously and the distal end 30 and tip 31 are positioned between vertebrae 36 to infuse the agent, drug or other fluid into either the epidural space 37 or the intrathecal space 38, depending on whether distal end 30 and tip 31 are passed through the arachnoid membrane 39. It should be understood that the particular placement of distal end 30 and tip 31 along the spinal column will depend on where specifically the agents, drugs or other fluids are desired to be delivered.

Figure 7:
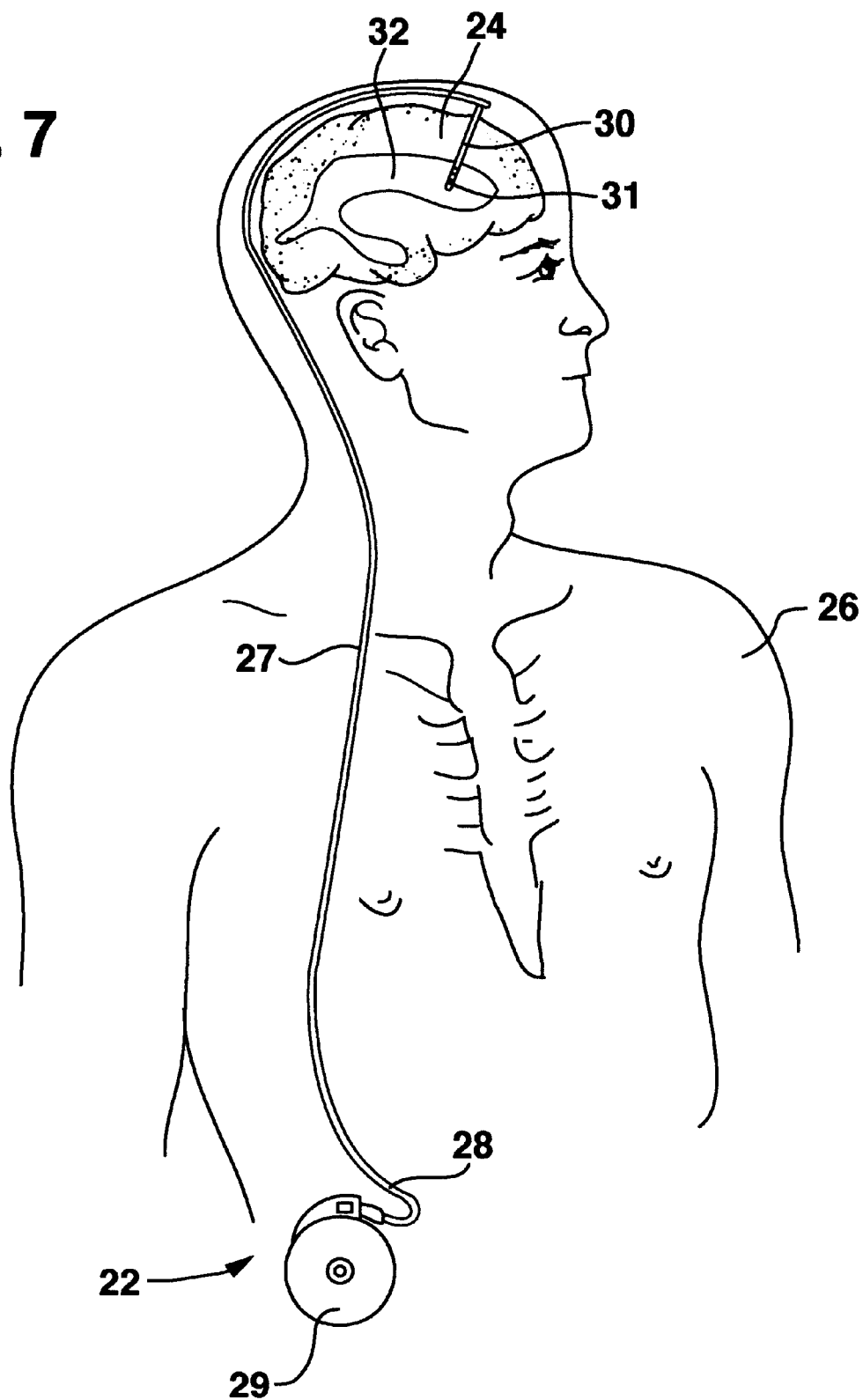
FIG. 7 depicts a preferred embodiment of the catheter system showing an alternate implantation in a human body.

FIG. 7 depicts a preferred embodiment of the catheter system 22 in another possible medical application, an intracerebroventricular placement, wherein catheter system 22 provides infusion of neurological agents or drugs directly into the brain 24 in a human body 26. Catheter system 22 comprises a catheter 27 which has a proximal end 28 coupled to an IIP 29 and a free distal end 30 for insertion into an organism, in this case, a human body 26. It should be understood that catheter system 22 could be also be used on non-human animals.

A catheter tip 31 is disposed at the extreme end of distal end 30. Tip 31 has a rounded leading exterior surface to minimize disruption during insertion. In the medical application portrayed in FIG. 7, distal end 30 is intracerebrally disposed so that tip 31 projects into the cerebral ventricle 32 of the brain 24. Distal end 30 is surgically implanted in the brain 24 and catheter 27 is subsequently tunnelled subcutaneously through the body 26 to the location in the body 26 where the IIP 29 will be implanted.

IIP 29 is ordinarily surgically implanted subcutaneously in the abdominal region of the body 26. IIP 29 may be any of a number of commercially available implantable infusion pumps such as, for example, the Synchromed pump, Model 8615, manufactured by Medtronic, Inc., Minneapolis, Minn. While an implantable IIP 29 is depicted, it should be understood to those skilled in the art that the device used to deliver agent to catheter 27 may be either implanted or extracorporeal.

Many modifications and variations may be made in the techniques and structures described and illustrated herein without departing from the spirit and scope of the present invention. Accordingly, the techniques and structures described and illustrated herein should be understood to be illustrative only and not limiting upon the scope of the present invention.

What is claimed is:

1. A method of making a catheter for delivering an agent, drug or fluid or a selected site within an organism comprising:

extruding an inner liner made of a material that is non-reactive with the agent, drug or fluid to be delivered to the selected site within the organism through the catheter, the inner liner having a lumen and a distal end;

extruding a tip having at least one orifice for engaging fluid communication with the lumen;

molding the tip to a desired configuration;

extruding a jacket, the jacket having a distal end;

sliding the jacket over the inner liner so that the distal end of the jacket extends distally beyond the distal end of the inner liner;

coupling the tip to the distal end of the inner liner; and, wherein the tip includes a radiographic marker attached to the distal end of the catheter, the radiographic marker comprising a semi-spherical portion with a cylindrical nipple emanating away therefrom, the cylindrical nipple being sized to fit snugly within the lumen and held in place by a biocompatible adhesive, the radiographic marker being made of a material opaque to x-rays.

2. The method of claim 1 wherein the step of extruding a jacket includes extruding a jacket made of a material that an agent, drug or other fluid to be delivered to a selected site within an organism exhibits detrimental sensitivity to.

3. The method of claim 1 wherein the step of extruding a jacket includes extruding a jacket made of a material that an agent, drug or other fluid to be delivered to a selected site within an organism may diffuse through.

4. The method of claim 1 wherein the step of extruding a jacket includes extruding a jacket made of a material that may allow a fluid to diffuse through the jacket from outside the catheter and affect an agent, drug or other fluid being delivered to a selected site within an organism.

5. The method of claim 1 wherein the step of coupling the tip includes the steps of:

applying a suitable biocompatible adhesive to the tip; and joining the tip to the jacket and inner liner.

6. A method of making a catheter for delivering an agent, drug or fluid to a selected site within an organism comprising:

extruding an inner liner made of a material that is non-reactive with the agent, drug or fluid to be delivered to the selected site within the organism through the catheter, the inner liner having a lumen and a distal end;

molding a tip to a desired configuration of a material that is non-reactive with the agent, drug or fluid to be delivered to the selected site within the organism through the catheter, the tip having at least one orifice for engaging fluid communication with the lumen;

extruding a jacket, the jacket having a distal end;

sliding the jacket over the jacket so that the distal end of the jacket extends distally beyond the distal end of the inner liner;

coupling the tip to the distal end of the inner liner; and, wherein the tip includes a radiographic marker attached to the distal end of the catheter, the radiographic marker comprising a semi-spherical portion with a cylindrical nipple emanating away therefrom, the cylindrical nipple being sized to fit snugly within the lumen and held in place by a biocompatible adhesive, the radiographic marker being made of a material opaque to x-rays.

7. The method of claim 6 wherein the step of extruding a jacket includes extruding a jacket made of a material that an agent, drug or other fluid to be delivered to a selected site within an organism exhibits detrimental sensitivity to.

8. The method of claim 6 wherein the step of extruding a jacket includes extruding a jacket made of a material that an agent, drug or other fluid to be delivered to a selected site within an organism may diffuse through.

9. The method of claim 6 wherein the step of extruding a jacket includes extruding a jacket made of a material that may allow a fluid to diffuse through the jacket from outside the catheter and affect an agent, drug or other fluid being delivered to a selected site within an organism.

10. The method of claim 6 wherein the step of coupling the tip includes the steps of:

applying a suitable biocompatible adhesive to the tip; and joining the tip to the jacket and inner liner.

* * * * *